United States Patent [19]

Teutsch et al.

[11] 4,272,530
[45] Jun. 9, 1981

[54] Δ1,3,5(10)-ESTRATRIENES

[75] Inventors: Jean G. Teutsch, Le Blanc-Mesnil; Daniel Philibert, La Varenne Saint-Hilaire, both of France

[73] Assignee: Roussel Uclaf, Paris, France

[21] Appl. No.: 867,486

[22] Filed: Jan. 6, 1978

[30] Foreign Application Priority Data

Jan. 13, 1977 [FR] France .............................. 77 00859

[51] Int. Cl.³ .................. A61K 31/58; A61K 31/56; C07J 1/00; C07J 3/00
[52] U.S. Cl. .......................... 424/238; 260/239.5; 260/239.55 C; 260/397.5; 424/241
[58] Field of Search .......................... 424/241, 238; 260/239.5, 397.5 A

[56] References Cited

U.S. PATENT DOCUMENTS

| | | | |
|---|---|---|---|
| 3,377,365 | 4/1968 | Baran | 260/397.5 |
| 3,465,010 | 9/1969 | Baran | 260/397.5 |
| 3,755,301 | 8/1973 | Baran et al. | 260/239.55 R |
| 3,922,292 | 11/1975 | Torelli et al. | 260/397.1 |
| 3,927,046 | 12/1975 | Van den Broek | 260/397.3 |
| 3,983,144 | 9/1976 | Leemhuis | 260/397.3 |

FOREIGN PATENT DOCUMENTS 1255345 12/1971 United Kingdom ................ 260/239.57

OTHER PUBLICATIONS

Fried, Organic Reactions in Steroid Chemistry, vol. 1, p. 314 (1972).

*Primary Examiner*—Ethel G. Love

*Attorney, Agent, or Firm*—Hammond & Littell, Weissenberger and Muserlian

[57] ABSTRACT

Novel 11β-substituted-Δ$^{1,3,5(10)}$-estratrienes of the formula

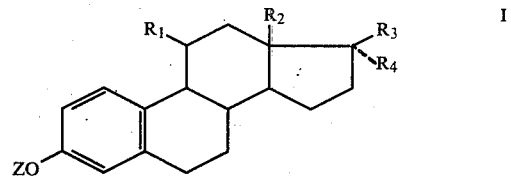

wherein $R_1$ is selected from the group consisting of optionally substituted unsaturated alkyl of 2 to 8 carbon atoms, optionally substituted aryl of 6 to 12 carbon atoms, optionally substituted aralkyl of 7 to 13 carbon atoms and heterocycle with at least one sulfur or oxygen heteroatom, $R_2$ is alkyl of 1 to 4 carbon atoms, Z is selected from the group consisting of hydrogen, alkyl of 1 to 12 carbon atoms and aralkyl of 7 to 9 carbon atoms, $R_3$ is selected from the group consisting of hydrogen, hydroxy, acyl of an organic carboxylic acid of 1 to 18 carbon atoms and acyloxy of an organic carboxylic acid of 1 to 18 carbon atoms and $R_4$ is selected from the group consisting of hydrogen, hydroxy, alkyl and alkoxy of 1 to 8 carbon atoms, acyloxy of an organic carboxylic acid of 1 to 8 carbon atoms and alkenyl and alkynyl of 2 to 8 carbon atoms, with the proviso that $R_1$ is not allyl when Z is hydrogen, $R_2$ is methyl, $R_3$ is hydroxy and $R_4$ is hydrogen having estrogenic activity and their preparation.

35 Claims, No Drawings

Δ1,3,5(10)-ESTRATRIENES

STATE OF THE ART

U.S. Pat. No. 3,922,292 describes 11β-substituted -Δ$^{1,3,5(10)}$-trienic steroids and U.S. Pat. No. 3,377,365 describes 11β-alkyl-Δ$^{1,3,5(10)}$-trienic steroids but neither one contains the 11β-substituent of formula I.

OBJECTS OF THE INVENTION

It is an object of the invention to provide the novel Δ$^{1,3,5(10)}$-trienes of formula I and a novel process for their preparation.

It is another object of the invention to provide novel estrogenic activity in warm-blooded animals.

These and other objects and advantages of the invention will become obvious from the following detailed description.

THE INVENTION

The novel 11β-substituted-Δ$^{1,3,5(10)}$-trienic steriods of the invention have the formula

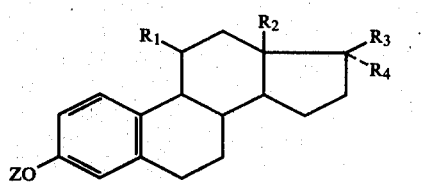

wherein $R_1$ is selected from the group consisting of optionally substituted unsaturated alkyl of 2 to 8 carbon atoms, optionally substituted aryl of 6 to 12 carbon atoms, optionally substituted aralkyl of 7 of 13 carbon atoms and heterocycle with at least one sulfur or oxygen heteroatom, $R_2$ is alkyl of 1 to 4 carbon atoms, Z is selected from the group consisting of hydrogen, alkyl of 1 to 12 carbon atoms and aralkyl of 7 to 9 carbon atoms, $R_3$ is selected from the group consisting of hydrogen, hydroxy, acyl of an organic carboxylic acid of 1 to 18 carbon atoms and acyloxy of an organic carboxylic acid of 1 to 18 carbon atoms and $R_4$ is selected from the group consisting of hydrogen, hydroxy, alkyl and alkoxy of 1 to 8 carbon atoms, acyloxy of an organic carboxylic acid of 1 to 8 carbon atoms and alkenyl and alkynyl of 2 to 8 carbon atoms, with the proviso that $R_1$ is not allyl when Z is hydrogen, $R_2$ is methyl, $R_3$ is hydroxy and $R_4$ is hydrogen.

Examples of $R_1$ are unsaturated alkyl such as vinyl, isopropenyl, allyl, 2-methyl-allyl and isobutenyl optionally substituted with thioalkyl of 1 to 4 carbon atoms such as methylthio or ethylthio or one or more halogens such as fluorine; aryl and aralkyl such as phenyl or benzyl optionally substituted in the o-, p- or m-position with alkoxy of 1 to 4 carbon atoms such as methoxy, one or more halogens such as chlorine or fluorine or —$CF_3$ or combinations thereof; and heterocycles such as thienyl, isothienyl or furyl.

Examples of $R_2$ are alkyl such as methyl, ethyl and propyl. Examples of $R_3$ and $R_4$ are alkoxy such as methoxy, ethoxy, propoxy, isopropoxy, butoxy, isobutoxy tert.-butoxy and pentyloxy or isopentyloxy acyl ($R_3$ only) or acyloxy of an organic carboxylic acid of 1 to 18 carbon atoms such as alkanoic acid such as formic acid, acetic acid, propionic acid, butyric acid, isobutyric acid or undecylic acid; hydroxyalkanoic acids such as hydroxyacetic acid; cycloalkylcarboxylic acids and cycloalkylalkanoic acids such as cyclopropylcarboxylic acid, cyclobutylcarboxylic acid, cyclopentylcarboxylic acid, cyclohexylcarboxylic acid cyclopentylacetic acid, cyclohexylacetic acid, cyclopentylpropionic acid or cyclohexylpropionic acid; benzoic acid; phenylalkanoic acids such as phenylacetic acid or phenylpropionic acid; or amino acids such as diethylaminoacetic acid or aspartic acid.

Further examples of $R_4$ are alkyl such as methyl, ethyl, propyl or butyl; alkenyl such as vinyl, allyl, 2-methylallyl or isobutenyl; and alkynyl such as ethynyl, 1-propynyl, 2-propynyl, 2-butynyl or butadiynyl.

Among the preferred compounds of formula I are those wherein $R_2$ is methyl, those wherein Z is hydrogen, those wherein $R_3$ is hydroxy, those wherein $R_4$ is alkynyl of 2 to 4 carbon atoms, especially ethynyl, those wherein $R_3$ is acyl of organic carboxylic acid of 1 to 8 carbon atoms, especially acetyl, those wherein $R_4$ is alkyl of 1 to 8 carbon atoms such as methyl, those wherein $R_1$ is saturated alkyl of 2 to 4 carbon atoms optionally substituted with thioalkyl of 1 to 4 carbon atoms or one or more fluorine atoms especially vinyl and allyl and those wherein $R_1$ is phenyl or benzyl optionally substituted on the ring with alkoxy of 1 to 4 carbon atoms as well as those wherein $R_1$ is thienyl.

Specific preferred compounds of formula I are 11β-vinyl-17α-ethynyl-Δ$^{1,3,5(10)}$-estratriene-3,17β-diol, 11β-allyl-17α-ethynyl-Δ$^{1,3,5(10)}$-estratriene-3,17β-diol, 11β-(p-methoxyphenyl)-17α-ethynyl-Δ$^{1,3,5(10)}$-estratriene-3,17β-diol, 11β-(o-methoxyphenyl)-17α-ethynyl-Δ$^{1,3,5(10)}$-estratriene-3,17β-diol, 11β-benzyl-17α-ethynyl-Δ$^{1,3,5(10)}$-estratriene-3,17β-diol, 11β-(2-thienyl)-17α-ethynyl-Δ$^{1,3,5(10)}$-estratriene-3,17β-diol and 11β-vinyl-17α-methyl-17β-acety-Δ$^{1,3,5(10)}$-estratriene-3-ol.

The novel process of the invention for the preparation of Δ$^{1,3,5(10)}$-estratrienes of formula I comprises reacting a compound of the formula

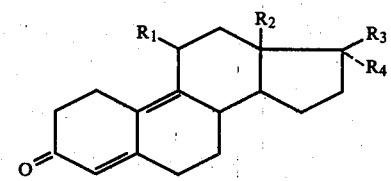

wherein $R_1$, $R_2$, $R_3$ and $R_4$ have the above definition with an aromatization agent and then with a saponification agent to obtain a compound of the formula

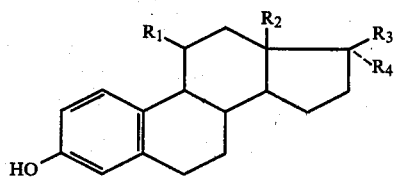

which may be reacted with an etherification agent to obtain the compound of formula I wherein Z is alkyl or aralkyl.

The aromatization agent is preferably an acyl halide such as acetyl bromide or an acid anhydride such as acetic anhydride but equally useful is a mixture of an acetyl halide and acetic anhydride. The subsequent saponification agent is preferably an alkali metal base such as sodium hydroxide, potassium hydroxide, sodium amide, potassium tert.-butylate or lithium acetylide in ethylene diamine and the reaction is preferably effected in a lower alkanol such as methanol or ethanol. The etherification agent is preferably an alkyl halide or aralkyl halide such as benzyl bromide or benzyl chloride.

The preferred process comprises using a mixture of acetyl bromide and acetic anhydride as the aromatization agent and sodium hydroxide as the saponification agent.

The starting compounds of formula II are new products which are prepared according to the process in commonly assigned Patent Application Ser. No. 867,485 filed on even date herewith comprising reacting a compound of the formula

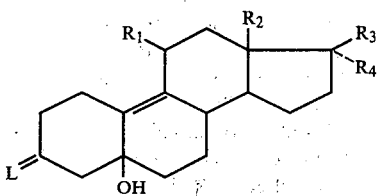

wherein $R_1$, $R_2$, $R_3$ and $R_4$ have the above definition and Z is a ketal group with a deshydration agent capable of freezing the ketone group.

The compounds of formula III are also novel products which are prepared according to the process in commonly assigned Patent Application Ser. No. 867,484 filed on even date herewith, now U.S. Pat. No. 4,147,695 comprising reacting a compound of the formula

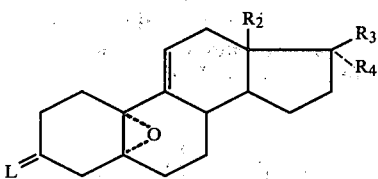

wherein L, $R_2$, $R_3$ and $R_4$ have the above definition with a compound of the formula $(R_1)_2$CuLi, $R_1$MgHal or $R_1$Li wherein $R_1$ has the above definition and Hal is a halogen in the presence of a catalytic amount of cuprous halide. The compounds of formula IV may be prepared by the process of French Pat. Nos. 1,550,974, 2,201,287 and 2,082,129.

The novel estrogenic compositions of the invention are comprised of an estrogenically effective amount of at least one compound of formula I and an inert pharmaceutical carrier or excipient. The compositions may be in the form of tablets, coated tablets, cachets, capsules, granules, emulsions, syrups, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, emulsifiers or dispersants and preservatives.

The compositions are useful for the treatment of menstrual troubles, with amenorrhea, dysmenorrhea or oligomenorrhea, for the treatment of functional problems of menopause, with paresthesia, palpitations, vertigo or the treatment of metabolic problems of menopause, with cutaneous trophicity or osteoporsis. The preferred compound is 11$\beta$-vinyl-17$\alpha$-ethynyl-$\Delta^{1,3,5(10)}$-estratriene-3$\alpha$,17$\beta$-diol.

The novel method of the invention of inducing estrogenic activity in warm-blooded animals, including humans, comprises administering to warm-blooded animals an estrogenically effective amount of at least one compound of formula I. The compounds may be administered orally, rectally, transcutaneously or intraveinously. The usual daily dose is 0,0002 to 0,010 mg/kg depending upon the specific compound or method of administration.

In the following examples there are described several preferred embodiments to illustrate the invention. However, it should be understood that the invention is not intended to be limited to the specific embodiments.

PREPARATION 1

22 mg of cuprous chloride were added at −10° C. to 4 ml of a solution of 1.5 M of vinyl magnesium bromide in tetrahydrofuran and then a solution of 1.30 g of 3-[(1,2-ethanediyl)-acetal] of 5$\alpha$,10$\alpha$-epoxy-17$\alpha$-trimethylsilyloxy-17$\beta$-cyano-$\Delta^{9(11)}$-estrene-3-one in 6 ml of tetrahydrofuran was added thereto. The mixture stood at −10° C. for 15 hours and was then poured into an aqueous ammonium chloride solution. The mixture was extracted with ether and the ether extracts were dried and evaporated to dryness. The residue was crystallized from ether to obtain 1.21 g of 3-[(1,2-ethanediyl)-acetal] of 11$\beta$-vinyl-17$\alpha$-trimethylsilyloxy-17$\beta$-cyano-$\Delta^9$-estrene-5$\alpha$-ol-3-one melting at 213° C.

PREPARATION 2

A solution of 26.8 g of allyl phenyl ether in 75 ml of ether was poured at −15° C. into a suspension of 5.6 g of lithium in 150 ml of tetrahydrofuran to obtain a solution of allyllithium. 83 ml of the said solution were added at −78° C. to a suspension of 5.15 g of a dimethylsulfide-cuprous bromide complex in 20 ml of tetrahydrofuran and after 15 minutes at −70° C., a solution of 4.13 g of 3-[(1,2-ethanediyl)-acetal] of 5$\alpha$,10$\alpha$-epoxy-17$\alpha$-trimethylsilyloxy-17$\beta$-cyano-$\Delta^{9(11)}$-estrene-3-one in 20 ml of tetrahydrofuran was added thereto. After 30 minutes, the mixture was poured into an aqueous ammonium chloride solution and the mixture was extracted with ether. The ether extracts were dried and evaporated to dryness to obtain 4.2 g of 3-[(1,2-ethanediyl)-acetal] of 11$\beta$-allyl-17$\alpha$-trimethylsilyloxy-17$\beta$-cyano-$\Delta^9$-estrene-5$\alpha$-ol-3-one with a specific rotation of $[\alpha]_D^{20} = -52° \pm 2°$ (c=0.6% in CHCl$_3$).

PREPARATION 3

Using the procedure of preparation 1, 3-[(1,2-ethanediyl)-acetal] of 5$\alpha$,10$\alpha$-epoxy-17$\alpha$-trimethylsilyloxy-17$\beta$-cyano-$\Delta^{9(11)}$-estrene-3-one and (p-methoxyphenyl)-magnesium bromide were reacted to obtain 3-[(1,2-ethanediyl)-acetal] of 11$\beta$-(p-methoxyphenyl)-17$\alpha$-trimethylsilyloxy-17$\beta$-cyano-$\Delta^9$-estrene-5$\alpha$-ol-3-one melting at 210° C. and having a specific rotation $(\alpha)_D^{20} = -12 \pm 2°$ (c=0.4% in CHCl$_3$).

PREPARATION 4

Using the procedure of preparation 1, the said acetal and (o-methoxyphenyl)-magnesium bromide were reacted to form 3-[(1,2-ethanediyl)-acetal] of 11$\beta$-(o-methoxyphenyl)-17$\alpha$-trimethylsilyloxy-17$\beta$-cyano-$\Delta^9$-estrene-5$\alpha$-ol-3-one with a specific rotation of $(\alpha)_D^{20} = -16.5° + 1$ (c=0.55% in CHCl$_3$).

PREPARATION 5

Using the procedure of preparation 1, the said acetal and benzyl magnesium bromide were reacted to form 3-[(1,2-ethanediyl)-acetal] of 11β-benzyl-17α-trimethylsilyloxy-17β-cyano-Δ$^9$-estrene-5α-ol-3-one melting at 160° C. and having a specific rotation of $(\alpha)_D^{20} = -86° \pm 3°$ (c=0.3% in CHCl$_3$).

PREPARATION 6

Using the procedure of preparation 1, the said acetal and (2-thienyl) magnesium bromide were reacted to obtain 3-[(1,2-ethanediyl)-acetal] of 11β-(2-thienyl)-17α-trimethylsilyloxy-17β-cyano-Δ$^9$-estrene-5α-ol-3-one melting at 260° C. and having a specific rotation of $(\alpha)_D^{20} = +34° \pm 2.5°$ (C=0.4% in CHCl$_3$).

PREPARATION 7

10 g of 3-[(1,2-ethanediyl)-acetal] of 17α-methyl-17β-acetyl-Δ$^{5(10),9(11)}$-estradiene-3-one (prepared by process of French Pat. No. 2,149,302) were added to a solution of 0.5 of pyridine in 240 ml of methylene chloride and after cooling the mixture to 0° C., 40 ml of a solution of hexafluoroacetone (30 mm) were added thereto. The mixture, after 10 minutes, was poured into an aqueous sodium bicarbonate-sodium thiosulfate solution. The mixture was extracted with methylene chloride and the organic extracts were dried and evaporated to dryness. The residue was crystallized from isopropyl ether to obtain 8.2 g of 3-[(1,2-ethanediyl)-acetal] of 5α, 10α-epoxy-17α-methyl-17β-acetyl-Δ$^{9(11)}$-estrene-3-one.

PREPARATION 8

6 g of a lithium acetylide-ethylene diamine complex were added to a solution of 3.5 g of 3-[(1,2-ethanediyl)-acetal] of 11β-vinyl-17α-trimethylsilyloxy-17β-cyano-Δ$^9$-estrene-5α-ol-3-one in 145 ml of ethylene diamine and the mixture stood overnight at 50°–60° C. The mixture was poured into ice water and the mixture was extracted with ether. The ether extracts were dried and evaporated to dryness and the residue was chromatographed over silica gel. Elution with a 6-4 petroleum ether-ethyl acetate mixture yielded 2.85 g of 3-[(1,2-ethanediyl)-acetal] of 11β-vinyl-17α-ethynyl-Δ$^9$-estrene-5lα,17β-diol-3-one melting at 160° C.

PREPARATION 9

Using the procedure of preparation 8, 2.4 g of 3-[(1,2-ethanediyl)-acetal] of 11β-allyl-17α-trimethylsilyloxy-17β-cyano-Δ$^9$-estrene-5α-ol-3-one were reacted to obtain 2.02 g of 3-[(1,2-ethanediyl)-acetal] of 11β-allyl-17α-ethynyl-Δ$^9$-estrene-5α,17β-diol-3-one.

PREPARATION 10

Using the procedure of preparation 8, 3.3 g of 3-[(1,2-ethanediyl)-acetal] of 11β-(p-methoxyphenyl)-17α-trimethylsilyloxy-17β-cyano-Δ$^9$-estrene-5α-ol-3-one was reacted to obtain 2.4 g of 3-[(1,2-ethanediyl)-acetal] of 11β-(p-methoxyphenyl)-17α-ethynyl-Δ$^9$-estrene-5α,17β-diol-3-one melting at 150° C.

PREPARATION 11

Using the procedure of preparation 8, 3-[(1,2-ethanediyl)-acetal] of 11β-(o-methoxyphenyl)-17α-trimethylsilyoxy-17β-cyano-Δ$^9$-estrene-5α-ol-3-one was reacted to obtain 3-[(1,2-ethanediyl)-acetal] of 11β-(o-methoxyphenyl)-17α-ethynyl-Δ$^9$-estrene-5α,17β-diol-3-one.

PREPARATION 12

Using the procedure of preparation 8, 2.8 g of 3-[(1,2-ethanediyl)-acetal] of 11β-benzyl-17α-trimethylsilyloxy-17β-cyano-Δ$^9$-estrene-5α-ol-3-one were reacted to obtain 2.05 g of 3-[(1,2-ethanediyl)-acetal] of 11β-benzyl-17α-ethynyl-Δ$^9$-estrene-5α,17β-diol-3-one melting at 152° C.

PREPARATION 13

Using the procedure of preparation 8, 3 g of 3-[(1,2-ethanediyl)-acetal] of 11β-(2-thienyl)-17α-trimethylsilyloxy-17β-cyano-Δ$^9$-estrene-5α-ol-3-one were reacted to obtain 2.37 g of 3-[(1,2-ethanediyl)-acetal] of 11β-(2-thienyl) -17α-ethynyl-Δ$^9$-estrene-5α,17β-diol-3-one melting at 140° C.

PREPARATION 14

150 mg of cuprous chloride were added at −40° C. to 17.6 ml of a solution of vinyl magnesium bromide and then a solution of 4 g of 3-[(1,2-ethanediyl)-acetal] of 5α,10α-epoxy-17α-methyl-17α-acetyl-Δ$^{9(11)}$-estrene-3-one in 15 ml of tetrahydrofuran was added thereto. After 2 hours at −40° C., the mixture was poured into an aqueous ammonium chloride solution and was extracted with ether. The ether extracts were dried and evaporated to dryness and the residue was crystallized from isopropyl ether to obtain 2.68 g of 3-[(1,2-ethanediyl)-acetal] of 11β-vinyl-17α-methyl-17β-acetyl-Δ$^9$-estrene-5α-ol-3-one.

PREPARATION 15

A mixture of 2.85 g of 3-[(1,2-ethanediyl)-acetal] of 11β-vinyl-17α-ethynyl-Δ$^9$-estrene-5α,17β-diol-3-one, 3 g of Redex CF (sulfonic acid resin) and 200 ml of 95% ethanol was refluxed for 30 minutes and was then filtered. The filtrate was evaporated to dryness and the residue was chromatographed over silica gel. Elution with a 6-4 petroleum ether-ethyl acetate mixture yielded 2.02 g of 11β-vinyl-17α-ethynyl-Δ$^{4,9}$-estradiene-17β-ol-3-one melting at 125° C.

PREPARATIONS 16 to 21

Using the procedure of preparation 15, the acetals of Table I were reacted to obtain the Δ$^{4,9}$-dienes of Table I.

TABLE I

| Starting Acetal | Final Product |
| --- | --- |
| 3-[(1,2-ethanediyl)-acetal] of 11β-allyl-17α-ethynyl-Δ$^9$-estrene-5α,17β-diol-3-one | 11β-allyl-17α-ethynyl-Δ$^{4,9}$-estradiene-17β-ol-3-one melting at 167° C. |
| 3-[(1,2-ethanediyl)-acetal] of 11β-(p-methoxyphenyl)-17α-ethynyl-Δ$^9$-estrene-5α,17β-diol-3-one | 11β-(p-methoxyphenyl)-17α-ethynyl-Δ$^{4,9}$-estradiene-17β-ol-3-one melting at 200° C. |
| 3-[(1,2-ethanediyl)-acetal] of 11β-(o-methoxyphenyl)-17α-ethynyl-Δ$^9$-estrene-5α,17β-diol-3-one | 11β-(o-methoxyphenyl)-17α-ethynyl-Δ$^{4,9}$-estradiene-17β-ol-3-one melting at 235° C. |
| 3-[(1,2-ethanediyl)-acetal] of 11β-benzyl-17α-ethynyl-Δ$^9$-estrene-5α,17β-diol-3-one | 11β-benzyl-17α-ethynyl-Δ$^{4,9}$-estradiene-17β-ol-3-one melting at 179° C. |
| 3-[(1,2-ethanediyl)-acetal] of 11β-(2-thienyl)-17α-ethynyl-Δ$^9$-estrene-5α,17β-diol-3-one | 11β-(2-thienyl)-17α-ethynyl-Δ$^{4,9}$-estradiene-17β-ol-3-one melting at 209° C. |
| 3-[(1,2-ethanediyl)-acetal] of 11β-vinyl-17α-methyl-17β-acetyl-Δ$^9$-estrene-5α-ol-3-one | 11β-vinyl-17α-methyl-17β-acetyl-Δ$^{4,9}$-estradiene-3-one melting at 105° C. |

EXAMPLE 1

11β-vinyl-17α-ethynyl-Δ$^{1,3,5(10)}$-estratriene-3,17β-diol 1.2 ml of acetic anhydride and 0.6 ml of acetyl bromide were added at 0° C. to a solution of 1.10 g of 11β-vinyl-17α-ethynyl-Δ$^{4,9}$-estradiene-17β-ol-3-one in 7.5 ml of methylene chloride and the temperature was allowed to rise to 25° C. The mixture was stirred for one hour at room temperature and was then poured into a mixture of ice, sodium bicarbonate and water. The mixture was extracted with ether and the ether extracts were evaporated to dryness. The oily residue was dissolved in 60 ml of methanol and 4.8 ml of sodium hydroxide solution were added thereto. The mixture was held at room temperature and was then neutralized and poured into water. The mixture was extracted with chloroform and the organic extracts were evaporated to dryness. The residue was chromatographed over silica gel and was eluted with a 6-4 petroleum ether-ethyl acetate mixture to obtain 0.742 g of 11β-vinyl-17α-ethynyl-Δ$^{1,3,5(10)}$-estratriene-3,17β-diol melting at 112° C.

EXAMPLES 2 to 7

Using the procedure of Example 1, the Δ$^{4,9}$-dienes of Table II were reacted to form the Δ$^{1,3,5(10)}$-trienes of Table II.

TABLE II

| Starting Compound | Final Product of Formula I | % Yield |
|---|---|---|
| 11β-allyl-17α-ethynyl-Δ$^{4,9}$-estradiene-17β-ol-3-one | 11β-allyl-17α-ethynyl-Δ$^{1,3,5(10)}$-estriene-3,17β-diol melting at 100~105° C. and having a specific rotation of $[\alpha]_D^{20} = +38° \pm 2.5°$ (c = 0.3% in CHCl$_3$) | 80% |
| 11β-(p-methoxyphenyl)-17α-ethynyl-Δ$^{4,9}$-estradiene-17β-ol-3-one | 11β-(p-methoxyphenyl)-17α-ethynyl-Δ$^{1,3,5(10)}$-estratriene-3,17β-diol melting at 263° C. and having a specific rotation of $[\alpha]_D^{20} = -142° \pm 4°$ (c = 0.4% in CHCl$_3$) | 50% |
| 11β-(o-methoxyphenyl)-17α-ethynyl-Δ$^{4,9}$-estradiene-17β-ol-3-one | 11β-(o-methoxyphenyl)-17α-ethynyl-Δ$^{1,3,5(10)}$-estradiene-3,17β-diol melting at 248° C. and having a specific rotation of $[\alpha]_D^{20} = -144° \pm 3°$ (c = 0.5% in CHCl$_3$) | |
| 11β-benzyl-17α-ethynyl-Δ$^{4,9}$-estradiene-17β-ol-3-one | 11β-benzyl-17α-ethynyl-Δ$^{1,3,5(10)}$-estratriene-3,17β-diol melting at 152° C. and having a specific rotation of $[\alpha]_D^{20} = -36° \pm 2°$ (c = 0.6% in CHCl$_3$) | 81% |
| 11β-(2-thienyl)-17α-ethynyl-Δ$^{4,9}$-estradiene-17β-ol-3-one | 11β-(2-thienyl)-17α-ethynyl-Δ$^{1,3,5(10)}$-estratriene-3,17β-diol melting at 154° C. and having a specific rotation of $[\alpha]_D^{20} = -56° \pm 2.5°$ (c = 0.6% in CHCl$_3$) | 89% |
| 11β-vinyl-17α-methyl-17β-acetyl-Δ$^{4,9}$-estradiene-3-one | 11β-vinyl-17α-methyl-17β-acetyl-Δ$^{1,3,5(10)}$-estratriene-3-ol melting at 210° C. and having a specific rotation of $[\alpha]_D^{20} = +109° \pm 3°$ (c = 0.5% in CHCl$_3$) | 85% |

EXAMPLE 8

Tablets were prepared containing 0.5 mg of the product of Example 1 and sufficient excipient of talc, starch and magnesium stearate to obtain a final weight of 120 mg.

PHARMACOLOGICAL DATA

A. Estrogenic Activity

The estrogenic activity was determined for 11β-vinyl-17α-ethynyl-1,3,5(10)-estratriene-3,17β-diol was determined by the hormonal receptor method of Raynaud et al. [J. Ster. Biochem., Vol. 6 (1975), p. 615–622]. Immature female mice aged 18 to 21 days old were sacrificed and the uterus was removed and homogenized in a buffered solution of 10 mm of tromethamine, 0.25 M of saccharose and a pH of 7.4 with hydrochloric acid. The homogenate was centrifuged at 105,000 g per hour and the surnageant or cytosol was adjusted to a dilution of 1/25 (weight/volume). The resulting solution was incubated at 25° C. for 5 hours in tubes with the same volume of cytosol with a fixed concentration of tritiated estradiol (designated at tritiated Product R) in the presence or not of an increasing concentration of radioinactive estradiol (designated as cold product R) or the test product. The radioactivity of the tritiated product R was determined in 2 hours by the technique of adsorption on carbondextran (1.25%–0.625%). The plots were the curves representing the percentage of tritiated product R as a function of the log of the concentration of cold product R or the test product and the I$_{50}$ straight line parallel to the axis of the abcisses and ordinates $$\frac{B}{T} = \frac{B/T \text{ Max.} + B/T \text{ Min.}}{2}$$

B/T max. is the percentage of tied tritiated product R when the product is not added and B/T min. is the percentage of tied tritiated product R when the maximum amount of cold product R is added. The intersections of these I$_{50}$ straight lines and the curves permit the determination of the values: CE—concentration of cold estradiol which inhibits by 50% the fixation of the tritiated product R and CX—concentration of test product which inhibits by 50% the fixation of tritiated product R. The relative affinity of the test product (ARL) was determined by the formula $$ARL = 100 \times \frac{CE}{CX}$$

and the results are reported in Table III.

TABLE III

| Product | ARL |
|---|---|
| Estradiol | 100 |
| Example 1 product | 240 |

The results of Table III show that the product of Example 1 has a greater affinity for specific uterine reception of estradiol than estradiol which means the product is an estrogen.

The estrogenic activity of the product of Example 1 was also determined by the method of Rubin [Endocrinology, Vol. 49 (1951), p. 429] in which female mice 19–21 days old received once a day for 3 days a subcutaneous injection of the test product. The animals were killed on the 4th day and the uterus was removed, dissected and weighed. The test product was administered in a volume of 0.1 ml of oily solution at doses of 0.01γ, 0.03γ, 0.09γ and 0.27γ. The results are reported in Table IV.

TABLE IV

| Dose in | Weight of uterus in mg |
|---|---|
| 0 | 11.4 ± 0.5 |
| 0.01 | 25.8 ± 1.7 |
| 0.03 | 90.1 ± 5.7 |
| 0.09 | 128.8 ± 12.1 |
| 0.27 | 107.6 ± 7.4 |

The results of Table IV show that the product has a clear uterotrophic activity.

Various modifications of the products and process of the invention may be made without departing from the spirit or scope thereof and it is to be understood that the invention is intended to be limited only as defined in the appended claims.

We claim:

1. A compound of formula

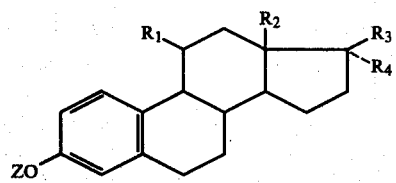

wherein $R_1$ is selected from the group consisting of unsaturated alkyl of 2 to 8 carbon atoms optionally substituted with a member selected from the group consisting of alkylthio of 1 to 4 carbon atoms and halogens, aryl of 6 to 12 carbon atoms and aralkyl of 7 to 13 carbons atoms optionally substituted with at least one member of the group consisting of alkoxy and alkylthio of 1 to 4 carbon atoms, halogens and -$CF_3$, thienyl, isothienyl and furyl, $R_2$ is alkyl of 1 to 4 carbon atoms, Z is selected from the group consisting of hydrogen, alkyl of 1 to 12 carbon atoms and aralkyl of 7 to 9 carbon atoms, $R_3$ is selected from the group consisting of hydrogen, hydroxy, acyl of an organic carboxylic acid of 1 to 18 carbon atoms and acyloxy of an organic carboxylic acid of 1 to 18 carbon atoms and $R_4$ is selected from the group consisting of hydrogen, hydroxy, alkyl and alkoxy of 1 to 8 carbon atoms, acyloxy of an organic carboxylic acid of 1 to 8 carbon atoms and alkenyl and alkynyl of 2 to 8 carbon atoms, with the proviso that $R_1$ is not allyl when Z is hydrogen, $R_2$ is methyl, $R_3$ is hydroxy and $R_4$ is hydrogen.

2. A compound of claim 1 wherein $R_2$ is methyl.
3. A compound of claim 1 wherein Z is hydrogen.
4. A compound of claim 1 wherein $R_3$ is hydroxy.
5. A compound of claim 1 wherein $R_4$ is alkynyl of 2 to 4 carbon atoms.
6. A compound of claim 1 wherein $R_4$ is ethynyl.
7. A compound of claim 1 wherein $R_3$ is acyl of an organic carboxylic acid of 1 to 8 carbon atoms.
8. A compound of claim 1 wherein $R_3$ is acetyl.
9. A compound of claim 1 wherein $R_4$ is alkyl of 1 to 8 carbon atoms.
10. A compound of claim 1 wherein $R_4$ is methyl.
11. A compound of claim 1 wherein $R_1$ is unsaturated alkyl of 2 to 4 carbon atoms optionally substituted with thioalkyl of 1 to 4 carbon atoms or at least one fluorine.
12. A compound of claim 1 wherein $R_1$ is vinyl.
13. A compound of claim 1 wherein $R_1$ is allyl.
14. A compound of claim 1 wherein $R_1$ is phenyl or benzyl optionally substituted on the phenyl ring with alkoxy of 1 to 4 carbon atoms.
15. A compound of claim 1 wherein $R_1$ is thienyl.
16. A compound of claim 1 selected from the group consisting of 11β-vinyl-17α-ethynyl-$\Delta^{1,3,5(10)}$-estratriene-3,17β-diol, 11β-allyl-17α-ethynyl-$\Delta^{1,3,5(10)}$-estratriene-3,17β-diol, 11β-(p-methoxyphenyl)-17α-ethynyl-$\Delta^{1,3,5(10)}$-estratriene-3,17α-diol, 11β-(o-methoxyphenyl)-17α-ethynyl-$\Delta^{1,3,5(10)}$-estratriene-3,17β-diol, 11β-benzyl-17α-ethynyl-$\Delta^{1,3,5(10)}$-estratriene-3,17β-diol, 11β-(2-thienyl)-17α-ethynyl-$\Delta^{1,3,5(10)}$-estratriene-3,17β-diol and 11β-vinyl-17α-methyl-17β-acetyl-$\Delta^{1,3,5(10)}$-estratriene-3-ol.
17. An estrogenic composition comprising an estrogenically effective amount of at least one compound of claim 1 and an inert pharmaceutical carrier.
18. The composition of claim 17 wherein the compound is 11β-vinyl-17α-ethynyl-$\Delta^{1,3,5(10)}$-estratriene-3,17β-diol.
19. A method of inducing estrogenic activity in warm-blooded animals comprising administering to warm-blooded animals an estrogenically effective amount of at least one compound of claim 1.
20. A method of claim 19 wherein $R_2$ is methyl.
21. A method of claim 19 wherein Z is hydrogen.
22. A method of claim 19 wherein $R_3$ is hydroxy.
23. A method of claim 19 wherein $R_4$ is alkynyl of 2 to 4 carbon atoms.
24. A method of claim 19 wherein $R_4$ is ethynyl.
25. A method of claim 19 wherein $R_3$ is acyl of an organic acid of 1 to 8 carbon atoms.
26. A method of claim 19 wherein $R_3$ is acetyl.
27. A method of claim 19 wherein $R_4$ is alkyl of 1 to 8 carbon atoms.
28. A method of claim 19 wherein $R_4$ is methyl.
29. A method of claim 19 wherein $R_1$ is unsaturated alkyl of 2 to 4 carbon atoms optionally substituted with thioalkyl of 1 to 4 carbon atoms or at least one fluorine.
30. A method of claim 19 wherein $R_1$ is vinyl.
31. A method of claim 20 wherein $R_1$ is allyl.
32. A method of claim 19 wherein $R_1$ is phenyl or benzyl optionally substituted on the phenyl ring with alkoxy of 1 to 4 carbon atoms.
33. A method of claim 19 wherein $R_1$ is thienyl.
34. The method of claim 19 wherein the compound is 11β-vinyl-17α-ethynyl-$\Delta^{1,3,5(10)}$-estratriene-3,17β-diol.
35.

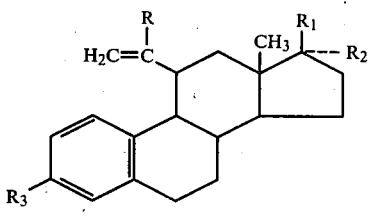

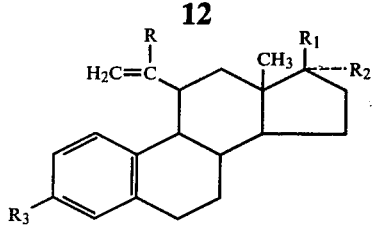

wherein R=hydrogen or methyl,
R$_1$=Hydroxy, acyloxy of an organic carboxylic acid of 1 to 18 carbons;
R$_2$=Hydrogen, alkyl of 1 to 4 carbon atoms, alkenyl of 2 to 4 carbons and alkynyl of 2 to 4 carbons and;
R$_3$=Hydroxy, alkoxy of 1 to 4 carbons and aralkoxy of 7 to 9 carbons.

* * * * * wherein R=hydrogen or methyl,
R$_1$=Hydroxy, acyloxy of an organic carboxylic acid of 1 to 18 carbons;
R$_2$=Hydrogen, alkyl of 1 to 4 carbon atoms, alkenyl of 2 to 4 carbons and alkynyl of 2 to 4 carbons and;
R$_3$=Hydroxy, alkoxy of 1 to 4 carbons and aralkoxy of 7 to 9 carbons.

* * * * *

UNITED STATES PATENT AND TRADEMARK OFFICE
CERTIFICATE OF CORRECTION

PATENT NO. :   4,272,530
DATED      :   June 9, 1981
INVENTOR(S) :  JEAN G. TEUTSCH ET AL.

It is certified that error appears in the above—identified patent and that said Letters Patent is hereby corrected as shown below:

Column 5, line 45:   "51α" should read -- 5α --.

Column 6, line 22:   "17α-acetyl" should read

-- 17β-acetyl --.

Column 10, line 5 of claim 16: "3,17α" should read -- 3,17β --.

Column 12:   Cancel said column.

Signed and Sealed this

Twentieth Day of October 1981

[SEAL]

Attest:

Attesting Officer

GERALD J. MOSSINGHOFF
Commissioner of Patents and Trademarks